United States Patent [19]
Jampani et al.

[11] Patent Number: 5,980,925
[45] Date of Patent: Nov. 9, 1999

[54] HIGH GLYCERIN CONTAINING ANTI-MICROBIAL CLEANSERS

[75] Inventors: Hunuman B. Jampani, Grapevine; Jerry L. Newman, Arlington, both of Tex.

[73] Assignee: Ethicon, Inc., Somerville, N.J.

[21] Appl. No.: 09/001,020

[22] Filed: Dec. 30, 1997

[51] Int. Cl.⁶ .................................................. A01N 25/00
[52] U.S. Cl. .................. 424/405; 424/401; 424/404; 424/78.03
[58] Field of Search ...................... 424/405, 401, 424/404, 70.12, 78.03; 510/426, 235; 514/844, 937, 943, 944

[56] References Cited

U.S. PATENT DOCUMENTS 5,719,113  2/1998  Fendler et al. ........................... 510/382

*Primary Examiner*—Jose' G. Dees
*Assistant Examiner*—Kathryne E. Shelborne
*Attorney, Agent, or Firm*—A. M. (Andy) Arismendi, Jr.; Tamsen Valoir

[57] ABSTRACT

Emulsions containing a dermal anchoring/substantive agent, such as glycerin, in high concentration enhance the activity of active ingredients, such as anti-microbial agents like chlorhexidine gluconate. Kits, compositions and methods pertaining to the same are provided. The invention finds application in cleansers such as hand washes, wound cleansers, body washes, mouthwashes, surgical scrubs, etc., and lotions, creams, foams and ointments. Specifically, one embodiment of the emulsion contains greater than 30% of an anchoring/substantive agent such as glycerin and an effective amount of chlorhexidine gluconate. Additionally, the product produced by the process of combining on the skin high glycerin and an anti-microbial is described.

26 Claims, No Drawings

HIGH GLYCERIN CONTAINING ANTI-MICROBIAL CLEANSERS

BACKGROUND OF THE INVENTION

1. Technical Field of the Invention

The present invention relates to compositions wherein a high concentration of a material with dermal anchoring/skin mechanical properties, such as high (more than 30%) glycerin, acts to enhance the effect of active ingredients, such as the anti-microbial agent chlorhexidine gluconate (CHG).

2. Background of the Invention

A variety of creams, lotions, washes and foams have been developed as an adjunct to protective gloves to sanitize and protect the skin from both the transmission and the receipt of infectious agents. These products contain a variety of wetting agents, fatty acids, solvents, emollients and other agents which act to protect the skin in a variety of ways. However, concern has been raised about the effect of these additives on a variety of active ingredients such as germicides (Larson, E., et al., *Effects of a Protective Coating Foam on Scrubbing and Gloving*, AMERICAN J. OF INFECTION CONTROL 21 (6): 297 (1993)). For example, it is taught that chlorhexidine and its derivatives are inhibited by a variety of ingredients including anionic surfactants, soaps, gums, sodium alginate, magnesium aluminum silicate, magnesium trisilicate, bentonite, talc, kaolin, high pH, 3% lecithin/polysorbate 80 and polysorbate: 80 (*Interaction between Cosmetic Ingredients and Preservatives*, COSMETICS & TOILETRIES 110: 81–86 (1995)). To address this concern, investigators have performed studies on the effect of various additives on the efficacy of active ingredients.

Kihara, for example, teaches that the bactericidal activity of chlorhexidine digluconate and benzalkonium chloride (BAC) decreases in the presence of other ingredients such as serum, polysaccharides, non-ionic surfactants, powdered milk, dried bovine serum albumin, fish powder and other organic substances (U.S. Pat. No. 5,017,617). Kihara states that most emollients used in cosmetics are nonionic surfactants or higher alcohols, so it is likely that they decrease the bactericidal activity of chlorhexidine digluconate and benzalkonium chloride. Therefore, Kihara tested a variety of emollients, including diesters of dibasic acids, triesters of citric acid or phosphoric acid, and polyglycerol (2 to 15 monomers), for their effect on chlorhexidine digluconate. Surprisingly, Kihara found that these di- and tri-esters enhanced, rather than inhibited, bactericidal activity. Kihara employs low concentrations of emollient (0.1–1.0%) in 50–95% ethanol and teaches that higher concentrations of emollient are to be avoided as producing a sticky feel. The mechanism of enhancement is not provided by Kihara, but it is possible that the long carbon chain, polar emollient molecules act on the bacterial membranes themselves, thus assisting the bactericidal effect of chlorhexidine digluconate.

Similarly, in JP 63057502 assigned to Saraya, the inventors found that in alcohol disinfecting solutions containing chlorhexidine gluconate (CHG) and an emollient selected from the group of diisopropyl adipate, diisobutyl adipate, higher fatty acid polyoxethylene glycerol and polyglycerol, the emollient enhanced the effect of CHG. Again, it may be that the long chain, fatty acids alone or in combination with CHG act on the bacterial membranes to assist the bactericidal effect of CHG alone.

Loosemore tested the effect of polyvinyl alcohol and propylene glycol on the germicidal activity of 0.6% CHG in a teat dip application (U.S. Pat. No. 5,641,498). Loosemore reported that neither ingredient adversely affected the activity of CHG. Although Loosemore's compositions contained 4% glycerin (also known as glycerol or glycerine), he neglected to compare the effect of this particular agent on the activity of CHG.

Others, however, have studied the effect of glycerin on particular active ingredients. Mundschenk, for example, studied the effect of glycerin on the efficacy of hydrogen peroxide as an anti-microbial agent in a dental cream (U.S. Pat. No. 5,512,278). Mundschenk reported that 20% glycerin did not negate the effectiveness of 3% hydrogen peroxide in this particular application. Similarly, Turck showed that addition of up to 10% glycerin did not decrease the anti-microbial activity of the disinfectant N,N-dimethyldodecanamine on liquid cultures of *Streptococcus agalactiae* or *Escherichia coli* (Turck, P. A., et al. *Mastitis: Effect of pH, Temperature and emollients on Disinfecting Action of N,N-dimethyldodecanamin*, J. DAIRY SCI. 65(10): 1987 (1982)), and Hicks showed that up to 6% glycerin did not affect the efficacy of chlorhexidine digluconate in a teat dip application (Hicks W. G., et al., *Evaluation of a Teat Dip of Chlorhexidine Digluconate (0.5%) with Glycerin (6%)*, J. DAIRY SCI. 64(11): 2266 (1981)).

Asaka teaches the use of 0.1–15% glycerin as an emollient used in combination with 25–80% lower alcohol, 0.01–4% cationic disinfectant such as CHG, and 1–40% amphoteric surfactant such as imidazolinium betaine (Australian Application No. AU-A-74370/94). Asaka notes that the emollients did not affect the disinfection by the cationic disinfectant, but states that concentrations higher than 15% may produce stickiness. Asaka's data shows that low levels of glycerin do not enhance the activity of CHG.

JP 61130210 assigned to San-Star showed that a paste containing CHG, 0.1–1% citric acid and 1–5% carrageenan improved the stability of CHG. A sample composition that also contained 30%. glycerin was provided.

To date no one has studied the effect of high levels of glycerin and similar compounds on the efficacy of active ingredients such as the anti-microbial chlorhexidine gluconate.

SUMMARY OF THE INVENTION

Broadly speaking, the invention is a wash solution comprising more than 30% of an anchoring agent and an effective amount of an active ingredient, preferably from about 0.1 to about 10%, wherein unless otherwise specified herein such percents are by weight based on the total weight of the wash solution. The anchoring agent is a simple polyol or is selected from the group consisting of 3 to 6 carbon polyols, 3 to 6 carbon aldoses, and 3 to 6 carbon ketoses, and their combinations and derivatives. The active ingredient is selected from the group consisting of anti-histamine, anti-inflammatory agents, analgesics, anesthetics, anti-perspirants, anti-dandruffs, anti-microbial agents, astringents, counter irritants, depigmenting agents, bleaching agents, and steroids.

More particularly, the anchoring agent may be selected from the group consisting of glycerol, propylene glycol, glyceraldehyde, dihydroxyacetone, 1,3-butylene glycol, 2,3-butylene glycol, erythritol, erythrose, erythrulose, ribose, sorbitol, mannitol, and inositol.

If the active ingredient is an anti-microbial, it may be chlorhexidine or its derivatives, such as chlorhexidine gluconate, chlorhexidine digluconate, chlorhexidine diacetate, chlorhexidine dihydrochloride, or it may be selected from the group consisting of nisin, bis-diguanides, polyhexamethylene biguanide (PHMB), benzalkonium chloride (BAC), benzethonium chloride (BZC), methylbenzethonium chloride, triclosan, triclocarban, tribromsalan, amyltricresols, parachlorometaxylenol (PCMX), phenol, iodine, nonylphenoxypoly (ethyleneoxy) ethanoliodine, poloxamer-iodine complex, undecoylium chloride iodine complex, bisquaternary ammonium compounds, polymeric quaternary ammonium compounds, alcohols, cationic peptides, organometaulic antiseptics, alkyl pyridinium salts such as cetyl pyridinium chloride (CPC), essential oils, and their combinations and derivatives.

Additional agents may be present in the wash solution of the invention including octadecene-1/maleic anhydride copolymer, organofluorinated modified silicone resins, polyvinyl pyrrolidone, hydrogenated copolymers of styrene and butadiene, film forming copolymers, copolymers of eicosene and vinyl pyrrolidone, copolymer of hexadecane and vinyl pyrrolidone, cellulosic ethers, 2-hydroxyethyl methacrylate homopolymer, cocodimethyl ammonium salt of hydrolyzate of wheat protein, guar hydroxy propyltrimonium chloride, hydroxypropylcellulose, lauryldimonium hydroxypropyl hydrolyzed collagen, lauryldimonium hydroxypropyl hydrolyzed wheat protein, polyquaternium-24 and hyaluronic acid, soluble reticulin and soluble wheat protein, stearyldimonium hydroxypropyl hydrolyzed collagen, acrylic/acrylate copolymers, behenoxy dimethicone, dimethicone copolyol phosphate, polydecene/polybutene copolymer, polymethacrylamidopropyl trimonium chloride, polymethylalkyl siloxane, and the like.

In another embodiment, the invention is a wash solution comprising more than 30% of a 3 to 6 carbon polyol and an effective amount of an anti-microbial agent, preferably from about 0.1 to about 10%. In another embodiment, the polyol has a backbone of 3 to 6 carbons and at least 2 alcohol groups. In a preferred embodiment, the polyol is glycerin and the anti-microbial agent is chlorhexidine gluconate (CHG). The anchoring agent, for example glycerin, is preferably present in an amount of at least 40% for example from about 40 about 80%, at least 50%, for example from about 50 to about 75%, or at least 60%. The anti-microbial agent may be present in an amount ranging from about 0.01 to about 10%, preferably from about 0.01 to 5%, and more preferably from about 0.1 to about 2%.

In another embodiment, the invention is a method of improving the efficacy of a polar anti-microbial agent on the skin, said method comprising the steps of treating the skin with a composition containing more than 30%, preferably at least 40%, of an anchoring agent; and washing the skin with an anti-microbial agent or composition containing the anti-microbial agent in an effective amount. The anchoring agents and anti-microbial agents are as described above. Although these steps may performed in any order or simultaneously, in a preferred method, the washing step is performed after the treating step.

The invention also includes kits for the anti-microbial treatment of skin. The kits contain at least a first container containing a first composition comprising more than 30% of an anchoring agent, as described above, and a second container containing a second composition comprising from about 0.1 to about 50% of an anti-microbial agent, as described above.

Furthermore, the invention includes a product produced by the process of treating the skin with a first composition containing more than 30% of an anchoring agent, as described above, and treating the skin with an effective amount of an anti-microbial agent, preferably present in an amount ranging from about 0.1 to about 50%, wherein the anti-microbials are as described above.

DETAILED DESCRIPTION OF THE INVENTION

To date, no one has studied the effect of high levels of glycerin on a variety of active ingredients. We have shown that high glycerin does not inhibit and even has a synergistic effect on a cationic anti-microbial agent, acting to preserve its effectiveness over longer periods of time than similar compositions without glycerin or with low levels of glycerin.

Though not wishing to be bound to any particular theory, it is hypothesized that high glycerin acts as a stratum corneum hydrator, creating a reservoir of glycerin in the stratum corneum. Studies have shown that high glycerin products actually deliver glycerin into the skin and increase the thickness of the entire stratum corneum (Appa, Y., et al, *Clinical Evaluations of Hand and Body Moisturizers that Heal Skin Dryness*, poster presentation at the 1992 American Academy of Dernatology, San Francisco, Dec. 6–7, 1992). It is believed that other materials with similar anchoring/substantive, hygroscopic and water solubility properties should have a similar effect, acting to penetrate the stratum corneum, hydrating it and providing a reservoir of water within which a polar active ingredient can dissolve/reside and be retained to increase its effectiveness. The effect may be even more pronounced where the active ingredient is both soluble in water and in the anchoring agent employed. This is true for the combination of CHG and glycerin because CHG is both water and glycerin soluble.

To test this hypothesis, the effect of similar polyols such as propylene glycol, butylene glycol, erythritol, xylitol, sorbitol, mannitol, and inositol, etc., and closely related molecules such as aldoses like glyceraldehyde, erythrose, threose, xylose, ribose, arabinose, lyxose, etc., and ketoses such as dihydroxyacetone, erythrulose, ribulose, xylulose, etc. were studied. Additional anchoring agents useful in the invention can be identified in the manner described in Example 1 by substituting such agent for CHG therein. Anchoring agents that enhance the activity of CHG by 20% are considered anchoring agents of this invention.

Likewise, the high anchoring agent content, for example high glycerin content, of this invention can be combined with and improved by the addition of other agents. Many polymeric materials with anchoring and substantive properties may be combined with the anchoring agents described above, for example glycerin, to provide improved retention and slow release of soluble active ingredients. For example, substantive agents include octadecene-1/maleic anhydride copolymer, organofluorinated modified silicone resins, polyvinyl pyrrolidone, hydrogenated copolymers of styrene and butadiene, film forming copolymers, copolymers of eicosene and vinyl pyrrolidone, copolymer of hexadecane and vinyl pyrrolidone, cellulosic ethers, 2-hydroxyethyl methacrylate homopolymer, cocodimethyl ammonium salt of hydrolyzate of wheat protein, guar hydroxy propyltrimonium chloride, hydroxypropylcellulose, lauryldimonium hydroxypropyl hydrolyzed collagen, lauryldimonium hydroxypropyl hydrolyzed wheat protein, polyquaternium-24 and hyaluronic acid, soluble reticulin and soluble wheat protein, stearyldimonium hydroxypropyl hydrolyzed collagen, acrylic/acrylate copolymers, Behenoxy dimethicone, dimethicone copolyol phosphate, polydecene/polybutene copolymer, polymethacrylamidopropyl trimonium chloride, polymethylalkyl siloxane, and the like.

However, where the anchoring agent composition is intended to be used where latex gloves might also be used, for example in a surgical setting, it is preferred that oil-based ingredients be kept to a minimum if possible. This is because petroleum and mineral oil based additives are known to compromise the structural integrity of latex. Thus, water soluble ingredients are preferred in this type of application.

Anti-microbial agents useful in the invention include nisin, bis-diguanides, chlorhexidine gluconate, chlorhexidine diguaconate, chlorhexidine diacetate, chlorhexidine dihydrochloride, polyhexamethylene biguanide, benzalkonium chloride, benzethonium chloride, methylbenzethonium chloride, cetyl pyridinium chloride, triclosan, triclocarban, tribromsalani, amyltricresols, parachlorometaxylenol, phenol, iodine, nonylphenoxypoly (ethyleneoxy) ethanoliodine, poloxameriodine complex, undecoylium chloride iodine complex, bisquaternary ammonium compounds, polymeric quaternary ammonium compounds, alcohols, cationic peptides, organometallic antiseptics, alkyl pyridinium salts, essential oils, and their combinations and derivatives. Likewise, a variety of simple alcohols may function in this regard, including but not limited to, ethanol, propanol, butanol, pentanol, 2-methyl-1-butanol, hexanol, 2-methyl-1-pentanol, 3-methyl-1-pentanol, 2-ethyl-1-butanol, 3,5,5-trimethyl-1-hexanol, heptanol, octanol, isooctyl alcohol, decanol, dodecanol, tridecanol, tetradecanol and the like.

Additional active ingredients useful in the invention can be identified in the manner described in the Example by substituting such active ingredients for CHG and anti-histamines, for example, diphenylhydramine and phenyltoloxamine; anti-inflammatory agents, for example, hydrocortisone; analgesics, for example capsaicin; anesthetics, for example benzocaine; anti-perspirants; anti-dandruffs; astringents, for example calamine, aluminum acetate and zinc oxide; counter irritants, for example menthol and camphor; depigmenting or bleaching agents; steroids; and the like. Active ingredients that have at least 20% increased activity when combined with 40% glycerin are included in this invention.

Active ingredient is defined herein as a pharmaceutically active ingredient that has increased substantive properties when combined with the anchoring agents below, meaning it penetrates into the skin, providing long lasting activity even after wash off.

Anchoring agent is defined herein as a hygroscopic agent that penetrates and remains in the upper layers of the skin (in other words a substantive agent), into which an active ingredient can be partitioned and retained with the anchoring agent against wash off. The anchoring agent provides for the slow release of an active ingredient, such as an anti-microbial.

Anti-microbial is defined herein as an agent that inhibits the growth of, or kills, organisms including bacteria, protozoans, viruses, prions, yeast, fungi, or other infectious agents, and has increased substantive properties when combined with the anchoring agents above, meaning it penetrates into the skin providing long lasting anti-microbial activity even after wash off.

High glycerin is defined herein as greater than 30% glycerin, preferably from about 35 to 100% glycerin, and more preferably from about 40 to about 80%, from about 50 to about 75%, or at least 60% glycerin, for example 60% glycerin (all percentages herein are w/w).

Simple Polyol is defined herein to exclude polymerized polyols, such as polyglycerol, and long chain (more than 3 carbons) esters of polyols such as fatty acid esters of glycerol.

Wash solution is defined herein as a solution that can be used before, during or after cleansing and may be hand washes, wound cleansers, body washes, mouthwashes, surgical scrubs, etc. in the form of liquids, lotions, creams, foams, gels, milks, and the like. Wash solution does not include soap bars.

EXAMPLE

The Synergistic Effect of High Glycerin on CHG

High (40%) glycerin and glycerin free formulations were tested for their effect on the germicidal effectiveness of a 4% solution of CHG per the technique described generally herein and adapted from Larson (Larson, E., et al., *Effects of a Protective Coating Foam on Scrubbing and Gloving*, AMERICAN J. OF INFECTION CONTROL 21 (6): 297 (1993)). Ten healthy subjects over the age of 18 but less than 70 were screened and admitted into the study. Insofar as possible, subjects were of mixed sex and age. All were free of clinically evident dermatoses or injuries to the hands or forearms.

During a 14-day pretest period, subjects avoided the use of medicated soaps, lotions, detergents and shampoos, as well as skin contact with solvents, acids and bases. Non-anti-microbial products were supplied to the subjects for their use throughout the pre-test period. This regimen allowed for the stabilization of the normal microbial populations of the hands.

Subjects participated in the study for 5 consecutive days. The first two days subjects had a baseline microbial count taken of both hands by the Glove Juice Procedure. For the baseline determination, hands were washed using a liquid nonmedicated baseline soap control (BABY SAN®, a HUNTINGTON™ product) according to standard surgical scrub procedures.

Subjects clipped fingernails to 2 mm free edge, if necessary. All jewelry was removed from hands and forearms. Subjects wet their hands, including two thirds (⅔) of the forearms, under running tap water 40±2° C. for thirty seconds. During this rinse, fingernails were cleaned with a nail cleaner. Hands were maintained higher than elbows during the wash procedure which was as follows. Hands and forearms were washed with 5 ml of baseline control soap for thirty (30) seconds using water as required to develop lather. Hands and forearms were rinsed thoroughly, removing all lather, for 30 seconds under running tap water at 40 ±2° C. Hands were not dried, but gloved wet. This was followed by the Glove Juice Procedure.

Glove Juice Procedure—Following the prescribed wash and rinse, powder free sterile latex gloves (FISHERBRAND® POWDER-FREE, STERILE, LATEX SURGICAL GLOVES) were donned. At the designated sampling times, 75 ml of sterile Stripping Suspending Fluid with neutralizers were placed into the glove. The wrist was secured, and an attendant massaged the hand through the glove in a standardized manner for 60 seconds. Aliquots of the glove juice were removed and serially diluted, $10^0$–$10^6$, in Butterfields Buffered Phosphate Solution.

Duplicate pour plates were prepared from each of these dilutions on Tryptic Soy Agar with 0.070% (w/v) lecithin and 0.5% Tween 80. Plates were incubated at 30°±2° C. for up to 72 hours. Those plates providing colony counts between 25 and 250 were counted and used. If the undiluted ($10^0$) plates gave an average count of 0, the average count was expressed as 1.00. This was done for mathematical reasons because the $\log_{10}$ of 0 is undefined, but the $\log_{10}$ of 1 is 0. The number of viable bacteria recovered was 75 X Dilution factor X mean plate count for the duplicate plates.

Subjects followed standard surgical scrub techniques using a solution of 4% CHG for 3 days. On day 3, after scrubbing the subjects applied 350 mg of either High Glycerin (HG) cream, 700 mg Glycerin Free (GF) lotion or no cream/lotion control. Microbial sampling was performed immediately after treatment or at 2 hours after treatment and the $\log_{10}$ reduction recorded as per Table 1. On day 4, no creams were used and on day 5, creams were applied prior to scrubbing. The results were as follows:

| Treatment | Test Day 3 HG/GF after scrub | | Test Day 4 no HG/GF | | Test Day 5 HG/GF before scrub | |
|---|---|---|---|---|---|---|
| | 0 hr | 2 hr | 0 hr | 2 hr | 0 hr | 2 hr |
| HG | 1.12 | 1.34 | 1.85 | 2.14 | 2.32 | 2.81** |
| GF | 1.03 | 1.46 | 2.02 | 2.28 | 2.01 | 2.17 |
| None | 1.23 | 1.50 | 1.63 | 2.16 | 1.93 | 2.18 |

**Significantly different when compared with the reference sample using the Student t test (p = 0.01).

Here the high glycerin cream product significantly enhanced the effect of CHG. It is noteworthy that enhancement of CHG occurs with low amounts of a high glycerin containing cream, but not with high amounts of a glycerin-free lotion.

The data was evaluated using several Analysis of Variance models and the Students t test. The data shows that the high (40%) glycerin cream enhanced the effect of CHG activity 2 hours post scrub on test day 5.

Glycerin is a known humectant that has beneficial effects on skin conditioning due to its effects on the status of water in at least the outer layers of the stratum corneum. This is probably the result of glycerin interactions with the lipid proteins in the stratum corneum, altering their water binding and/or hydrophilic properties. Due to this phenomena, as glycerol increases in the skin, so does water increase to form a reservoir in which water soluble active ingredients, such as CHG, can be dissolved and retained against wash off. Additionally, where the active ingredient is itself soluble in glycerin, the enhancement effect is further increased. These effects may explain the mode of action of glycerin enhancement of CHG activity.

The enhancement is best seen when the skin is first treated with a dermal anchoring agent before washing with CHG. This is because a reservoir has been created into which the maximum amount of CHG can diffuse. When the dermal agent is used after the CHG wash, there is less CHG present to diffuse into the skin with the dermal anchoring agent, most of the CHG having already been rinsed off due to lack of a dermal anchoring agent. However, it is anticipated that the enhancement effect will occur whether the dermal anchoring agent is used simultaneously with, before or after the CHG wash, because this is always some amount of CHG retained on the skin even after rinsing.

The invention has been described in an illustrative manner, and it is to be understood that the terminology which has been used is intended to be in the nature of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A wash solution comprising:
   (a) more than 30% of an anchoring agent,
      wherein the anchoring agent is selected from the group consisting of 3 to 6 carbon polyols, 3 to 6 carbon aldoses, and 3 to 6 carbon ketoses, and their combinations and derivatives;
   (b) from about 0.01% to about 10% active ingredient,
      wherein the active ingredient is selected from the group consisting of anti-histamines, anti-inflammatory agents, analgesics, anesthetics, anti-perspirants, anti-dandruffs, anti-microbial agents, astringents, counter-irritants, depigmenting agents, bleaching agents, and steroids.

2. The wash solution of claim 1, wherein the active ingredient is an anti-microbial agent.

3. The wash solution of claim 1, wherein the anchoring agent is a 3 to 6 carbon polyol.

4. The wash solution of claim 3, wherein the polyol is a polyol which has a backbone of 3 to 6 carbons and at least two hydroxyl groups.

5. The wash solution of claim 4, wherein the active agent is an anti-microbial agent.

6. The wash solution of claim 5,
   wherein the polyol is selected from the group consisting of glycerin, propylene glycol, butylene glycol and combinations thereof; and
   wherein the anti-microbial agent is a chlorhexidine derivative.

7. The wash solution of claim 5,
   wherein the polyol is glycerin; and
   wherein the anti-microbial agent is chlorhexidine gluconate.

8. The wash solution of claim 3,
   wherein the 3 to 6 carbon polyol is selected from the group consisting of glycerin, propylene glycol, 1,3-butylene glycol, 2,3-butylene glycol and combinations thereof; and
   wherein the active ingredient is an anti-microbial agent selected from the group consisting of chlorhexidine gluconate, chlorhexidine digluconate, chlorhexidine diacetate, chlorhexidine dihydrochloride and combinations thereof.

9. The wash solution of claim 5,
   wherein the anti-microbial agent is a chlorhexidine derivative.

10. The wash solution of claim 9,
    wherein the chlorhexidine derivative is chlorhexidine gluconate.

11. The wash solution of claim 5,
    wherein the anti-microbial agent is nisin.

12. The wash solution of claim 5,
    wherein the anchoring agent is selected from the group consisting of glycerol, propylene glycol, glyceraldehyde, dihydroxyacetone, 1,3-butylene glycol, 2,3-butylene glycol, erythritol, erythrose, erythrulose, sorbitol, mannitol, and inositol; and
    wherein the anti-microbial agent is selected from the group consisting of nisin, bis-diguanides, chlorhexidine gluconate, chlorhexidine digluconate, chlorhexidine diacetate, chlorhexidine dihydrochloride, polyhexamethylene biguanide, benzalkonium chloride, benzethonium chloride, methylbenzethonium chloride, cetyl pyridinium chloride, triclosan, triclocarban, tribromsalan, amyltricresols, parachlorometaxylenol, phenol, iodine, nonylphenoxypoly (ethyleneoxy) ethanoliodine, poloxamer-iodine complex, undecoylium chloride iodine complex, bisquaternary ammonium compounds, polymeric quaternary ammonium compounds, cationic peptides, organometallic antiseptics, alkyl pyridinium salts, essential oils, ethanol, propanol, butanol, pentanol, 2-methyl-1- butanol, hexanol, 2-methyl-1-pentanol, 3-methyl-1-pentanol, 2-ethyl-1-butanol, 3,5,5-trimethyl-10-hexanol, heptanol, octanol, isooctyl alcohol, decanol, dodecanol, tridecanol, tetradecanol and their combinations and derivatives.

13. The wash solution of claim 1, further comprising an agent selected from the group consisting of octadecene-1/maleic anhydride copolymer, organofluorinated modified silicone resins, polyvinyl pyrrolidone, hydrogenated copolymers of styrene and butadiene, film forming copolymers, copolymers of eicosene and vinyl pyrrolidone, copolymer of hexadecane and vinyl pyrrolidone, cellulosic ethers, 2-hydroxyethyl methacrylate homopolymer, cocodimethyl ammonium salt of hydrolyzate of wheat protein, guar hydroxy propyltrimonium chloride, hydroxypropylcellulose, lauryldimonium hydroxypropyl hydrolyzed collagen, lauryldimonium hydroxypropyl hydrolyzed wheat protein, polyquaternium-24 and hyaluronic acid, soluble reticulin and soluble wheat protein, stearyldimonium hydroxypropyl hydrolyzed collagen, acrylic/acrylate copolymers, Behenoxy dimethicone, dimethicone copolyol phosphate, polydecene/polybutene copolymer, polymethacrylamidopropyl trimonium chloride, and polymethylalkyl siloxane.

14. The wash solution of claim 1,
wherein the anchoring agent is present in an amount of at least 40% of the wash solution.

15. The wash solution of claim 1, wherein the anchoring agent is present in an amount ranging from about 40% to about 80% of the wash solution.

16. The wash solution of claim 15, wherein the anti-microbial agent is present in an amount ranging from about 0.01% to about 5% of the wash solution.

17. The wash solution of claim 16, wherein the anchoring agent is glycerin and the anti-microbial agent is chlorhexidine gluconate.

18. A method of improving the efficacy of a polar anti-microbial agent on the skin, said method comprising the steps of:
treating the skin with a composition containing more than 30% of an anchoring agent; and
washing the skin with an anti-microbial agent.

19. The method of claim 18,
wherein the anchoring agent is selected from the group consisting of glycerol, propylene glycol, glyceraldehyde, dihydroxyacetone, 1,3-butylene glycol, 2,3-butylene glycol, erythritol, erythrose, erythrulose, sorbitol, mannitol, and inositol; and
wherein the anti-microbial agent is selected from the group consisting of nisin, bis-diguanides, chlorhexidine gluconate, chlorhexidine digluconate, chlorhexidine diacetate, chlorhexidine dihydrochloride, polyhexamethylene biguanide, benzalkonium chloride, benzethonium chloride, methylbenzethonium chloride, cetyl pyridinium chloride, triclosan, triclocarban, tribromsalan, amyltricresols, parachlorometaxylenol, phenol, iodine, nonylphenoxypoly (ethyleneoxy) ethanoliodine, poloxamer-iodine complex, undecoylium chloride iodine complex, bisquaternary ammonium compounds, polymeric quaternary ammonium compounds, cationic peptides, organometallic antiseptics, alkyl pyridinium salts, essential oils, ethanol, propanol, butanol, pentanol, 2-methyl-1-butanol, hexanol, 2-methyl-1-pentanol, 3-methyl-1-pentanol, 2-ethyl-1-butanol, 3,5,5-trimethyl-10-hexanol, heptanol, octanol, isooctyl alcohol, decanol, dodecanol, tridecanol, tetradecanol and their combinations and derivatives.

20. The method of claim 18, wherein the anchoring agent is glycerin and the anti-microbial agent is a chlorhexidine derivative or nisin.

21. The method of claim 18, wherein the first step is the step of washing with the anti-microbial agent.

22. The method of claim 18, wherein the first step is the step of treating the skin with the composition containing the anchoring agent.

23. A kit used for the anti-microbial treatment of skin, said kit comprising:
a first composition comprising more than 30% of an anchoring agent,
wherein the anchoring agent is selected from the group consisting of 3 to 6 carbon polyols, 3 to 6 carbon aldoses, and 3 to 6 carbon ketoses, and their combinations and derivatives; and
a second composition comprising from about 0.1% to about 50% of an anti-microbial agent,
wherein the anti-microbial agent is selected from the group consisting of nisin, bis-diguanides, chlorhexidine gluconate, chlorhexidine digluconate, chlorhexidine diacetate, chlorhexidine dihydrochloride, polyhexamethylene biguanide, benzalkonium chloride, benzethonium chloride, methylbenzethonium chloride, cetyl pyridinium chloride, triclosan, triclocarban, tribromsalan, amyltricresols, parachlorometaxylenol, phenol, iodine, nonylphenoxypoly (ethyleneoxy) ethanoliodine, poloxamer-iodine complex, undecoylium chloride iodine complex, bisquaternary ammonium compounds, polymeric quaternary ammonium compounds, cationic peptides, organometallic antiseptics, alkyl pyridinium salts, essential oils, ethanol, propanol, butanol, pentanol, 2-methyl-1-butanol, hexanol, 2-methyl -1-pentanol, 3-methyl-1-pentanol, 2-ethyl-1-butanol, 3,5,5-trimethyl-10-hexanol, heptanol, octanol, isooctyl alcohol, decanol, dodecanol, tridecanol, tetradecanol and their combinations and derivatives.

24. The kit of claim 23, wherein the anchoring agent is glycerin and the anti-microbial agent is a chlorhexidine derivative or nisin.

25. A product produced by the process of:
treating the skin with a first composition containing more than 30% of an anchoring agent,
wherein the anchoring agent is selected from the group consisting of 3 to 6 carbon polyols, 3 to 6 carbon aldoses, and 3 to 6 carbon ketoses, and their combinations and derivatives; and
treating said skin with a second composition containing from about 0.1 to about 50% of an anti-microbial agent,
wherein the anti-microbial agent is selected from the group consisting of nisin, chlorhexidine gluconate, chlorhexidine digluconate, chlorhexidine diacetate, chlorhexidine dihydrochloride, benzalkonium chloride, benzethonium chloride, methylbenzethonium chloride, cetyl pyridinium chloride, triclosan, triclocarban, tribromsalan, amyltricresols, parachlorometaxylenol, phenol, iodine, nonylphenoxypoly (ethyleneoxy) ethanoliodine, poloxamer-iodine complex, undecoylium chloride iodine complex, bisquaternary ammonium compounds, polymeric quaternary ammonium compounds, cationic peptides, organometallic antiseptics, alkyl pyridinium salts, essential oils, ethanol, propanol, butanol, pentanol, 2-methyl-1-butanol, hexanol, 2-methyl-1-pentanol, 3-methyl-1-pentanol, 2-ethyl-1-butanol, 3,5,5-trimethyl-10-hexanol, heptanol, octanol, isooctyl alcohol, decanol, dodecanol, tridecanol, tetradecanol and their combinations and derivatives.

26. The product of claim 25, wherein the anchoring agent is glycerin and the anti-microbial is a chlorhexidine derivative.

* * * * *